(12) United States Patent
Willis et al.

(10) Patent No.: US 6,679,989 B2
(45) Date of Patent: Jan. 20, 2004

(54) INTEGRAL, THRU-BORE, DIRECT COUPLED HIGH PRESSURE LIQUID CHROMATOGRAPHY GUARD COLUMN

(75) Inventors: Frank Willis, Wenonah, NJ (US); Clyde Machamer, Elkton, MD (US)

(73) Assignee: Agilent Technologies, Inc., Palo Alto, CA (US)

( * ) Notice: Subject to any disclaimer, the term of this patent is extended or adjusted under 35 U.S.C. 154(b) by 46 days.

(21) Appl. No.: 09/870,780

(22) Filed: Jun. 1, 2001

(65) Prior Publication Data

US 2002/0179513 A1 Dec. 5, 2002

(51) Int. Cl.⁷ .............................................. B01D 15/08
(52) U.S. Cl. ........................ 210/198.2; 210/656; 96/101
(58) Field of Search .............................. 210/198.2, 656; 96/101; 422/70

(56) References Cited

U.S. PATENT DOCUMENTS

| | | | | |
|---|---|---|---|---|
| 3,483,986 A | * | 12/1969 | Wright | 210/198.2 |
| 3,682,315 A | * | 8/1972 | Haller | 210/198.2 |
| 3,763,879 A | * | 10/1973 | Jaworek | 210/198.2 |
| 3,878,099 A | * | 4/1975 | Ogle | 210/198.2 |
| 3,902,849 A | * | 9/1975 | Barak | 210/198.2 |
| 4,080,294 A | * | 3/1978 | Edwards | 210/232 |
| 4,283,280 A | * | 8/1981 | Brownlee | 210/198.2 |
| 4,313,828 A | * | 2/1982 | Brownlee | 210/198.2 |
| 4,451,364 A | * | 5/1984 | Higgins | 210/198.2 |
| 4,457,846 A | * | 7/1984 | Munk | 210/198.2 |
| 4,551,249 A | * | 11/1985 | Shackelford | 210/198.2 |
| 4,565,632 A | * | 1/1986 | Hatch | 210/198.2 |
| 4,636,316 A | * | 1/1987 | Harris | 210/198.2 |
| 4,655,917 A | * | 4/1987 | Shackelford | 210/198.2 |
| 4,719,011 A | * | 1/1988 | Shalon et al. | 210/198.2 |
| 4,732,687 A | * | 3/1988 | Muller | 210/198.2 |
| 4,737,284 A | * | 4/1988 | Hauke | 210/198.2 |
| 4,806,238 A | * | 2/1989 | Sattler | 210/198.2 |
| 4,876,005 A | * | 10/1989 | America | 210/198.2 |
| 5,137,628 A | * | 8/1992 | Hart | 210/198.2 |
| 5,141,635 A | * | 8/1992 | LePlang | 210/198.2 |
| 5,324,427 A | * | 6/1994 | Traveset-Masanes | 210/198.2 |
| 5,738,785 A | * | 4/1998 | Brown | 210/232 |
| 5,863,428 A | * | 1/1999 | Ma et al. | 210/198.2 |
| 6,068,767 A | * | 5/2000 | Garguilo | 210/198.2 |
| 6,139,733 A | * | 10/2000 | Hargro | 210/198.2 |

OTHER PUBLICATIONS

Snyder, Introduction to Modern Liquid Chromatography, 1979, John Wiley, p. 6.*
Agilent ZORBAX Reliance Cartridge–Columns, Datasheet, Agilent Technologies, Inc., (undated) pp. 1–4.
Liquid Chromatography, Columns, Zorbax Reliance Cartridge–Columns, Hewlett–Packard Co., Mar. 1999 pp. 1–4.
Liquid Chromatography Column Data, ZORBAX Reliance Cartridge–Column Series, Rockland Technologies, Inc., Feb. 1996 pp. 1–4.
ZORBAX Chromatography Products, ZORBAX Reliance Cartridges, p. 9, DuPont Co., (undated) pp. 1–2.
Chemical Analysis Consumables and Accessories, Reliance Cartridge System, p. 279, Hewlett–Packard Co., 1998/1999 pp. 1–2.

* cited by examiner

*Primary Examiner*—Ernest G. Therkorn

(57) ABSTRACT

Guard columns for high-pressure liquid chromatography (HPLC) apparatuses. These guard columns can be removable and/or metallic guard columns. Further, all of the outlet of the guard column can substantially engage the inlet of an HPLC column in the HPLC apparatus. Also, an HPLC apparatus that includes a guard column, a hand-tightened top end fitting at a first end of the HPLC apparatus and a hand-tightened bottom end fitting at a second end of the HPLC apparatus.

11 Claims, 5 Drawing Sheets

INTEGRAL, THRU-BORE, DIRECT COUPLED HIGH PRESSURE LIQUID CHROMATOGRAPHY GUARD COLUMN

BACKGROUND OF THE INVENTION

1. Field of the Invention

The present application relates generally to the field of guard columns for high-pressure liquid chromatography (HPLC) devices. Guard columns are generally used to protect HPLC columns from physical or chemical contamination.

2. Description of the Related Art

High-pressure liquid chromatography (HPLC) is a process used for separating one or more compounds from a chemical mixture. The HPLC process consists of passing the mixture through a stationary packing material, under the influence of a high-pressure transport liquid, and separating the compounds by selective affinity, sieving, absorption or partition. The packing is typically housed within a thru-bored section of a body of a column and is typically held in place by frits at either end of the body.

FIG. 1 illustrates a typical HPLC apparatus 10 according to the related art wherein a chemical mixture is injected into the HPLC apparatus 10 through an injection apparatus 300. The mixture first passes through the frits 120, 140 and packing 115 of a guard column 30. Then, the mixture is "funneled" through a narrow opening of a capillary connector 40 that is located between the guard column 30 and an HPLC column 20. From that point, the mixture flows through the frits 180, 200 and packing 170 of the HPLC column 20 and the components of the mixture can then travel through an exit apparatus 340 after which they can be measured, collected, redirected or disposed of.

The typical HPLC apparatus 10 illustrated in FIG. 1 shows the guard column 30 contained within a housing 45 and held in place by a threaded top end fitting 310. The top end fitting 310 is screwed onto an end of the housing 45. Because of the extreme pressures sometimes used to conduct HPLC processes (e.g., pressures up to and above 6,000 pounds per square inch (psi)), the top end fitting 310 is typically screwed to the housing 45 using wrenches or other methods of supplying high torque.

The injection apparatus 300 through which the mixture enters the HPLC apparatus 10 is sheathed within the top end fitting 310. A small region of the top end fitting 310 can form a top end fitting pathway 12 through which the mixture travels before flowing into the guard column 30.

The guard column 30 is positioned between the top end fitting 310 and the housing 45. To prevent leaks, a guard column top seal 90 is placed between the guard column 30 and the top end fitting 310 and a guard column bottom seal 70 is placed between the guard column 30 and the housing 45.

The guard column 30 is removable and replaceable. To remove the guard column 30, the top end fitting 310 is unscrewed from the housing 45 and the guard column 30 is pulled out. The guard column 30 can then be inspected and, if necessary, replaced. An advantage of a replaceable guard column 30 is that the HPLC column 20, which is substantially more expensive than the guard column 30, does not have to be replaced as often, if ever. The guard column 30 traps impurities or particulates in the sample mixture or in the transport liquid before the impurities or particulates can reach the HPLC column 20 and thereby extends the operable lifetime of the HPLC column 20.

The capillary connector 40 can be a piece of tubing or other device that connects the guard column 30 to the HPLC column 20. It is, according to FIG. 1, held in place by a top capillary fitting 22 and a bottom capillary fitting 23.

The capillary connector 40 abruptly changes the cross-sectional area of the path of the mixture by forcing the mixture to flow from the thru-bore section of the guard column 30 to the relatively narrow opening of the capillary connector 40. Then, the mixture passes through a relatively large thru-bore section of the HPLC column 20. The sudden changes in the cross-sectional area of the flow path disrupt the flow of the mixture, cause unwanted mixing and blending of the mixture, and lower the capability of the HPLC column 20 to separate compounds from the mixture (i.e., causes band-spreading).

An improvement to the HPLC apparatus 10 design depicted in FIG. 1 exists in the related art. This improvement eliminates the capillary connector 40 by making the guard column 30 "integral" to the HPLC column 20.

FIG. 2 illustrates such an alternative HPLC apparatus 10, according to the related art, wherein a chemical mixture is injected into the HPLC apparatus 10 through an injection apparatus 300. The mixture first passes through the frits 120, 140 and packing 115 of a guard column 30 that sits in a guard column housing 45. Then, the mixture is "funneled" through a narrow opening that is located on the exit end of the guard column housing 45. From that point, the mixture flows through the frits 180, 200 and packing 170 of the HPLC column 20 and the components of the mixture can then travel through an exit apparatus 340, after which they can be measured, collected, redirected or disposed of.

The components of the HPLC apparatus 10 illustrated in FIG. 2 are contained within an assembly comprised of an externally threaded bottom end fitting 360 and an internally threaded top end fitting 310. This assembly is held in place by engaging two upper grommets 350 that fit into an upper groove 380 that is machined into the outer wall of the HPLC column 20. Because of the extreme pressures sometimes used to conduct HPLC processes (e.g., pressures up to and above 6,000 psi), the top end fitting 310 and the bottom end fitting 360 are typically screwed together using wrenches or other methods of supplying high torque.

The injection apparatus 300 through which the mixture enters the HPLC apparatus 10 is sheathed within the top end fitting 310. A small region of the top end fitting 310 can form a pathway 12 through which the mixture travels before flowing into the guard column 30.

The guard column 30 is enclosed in a guard column housing 45 and positioned between the top end fitting 310 and the HPLC column 20. To prevent leaks, a guard column top seal 90 is placed in the guard column housing 45 above the top end of the guard column 30. This guard column top seal 90 mates with the exit end of the top end fitting 310 to form a leak-tight seal. An HPLC column top seal 100 is placed inside the HPLC column 20 to mate with the exit end of the guard column housing 45 to form a leak-tight seal.

The guard column 30 and the guard column housing 45 are removable and replaceable. To remove the guard column 30 and the guard column housing 45, the internally threaded top end fitting 310 is unscrewed from the externally threaded bottom end fitting 360 and the guard column 30 and the guard column housing 45 are pulled out. The guard column 30 can then be inspected and, if necessary, the guard column 30 and the guard column housing 45 can be replaced.

The guard column housing 45 abruptly changes the cross-sectional area of the path of the mixture by forcing the mixture to flow from the thru-bore section of the guard column 30 to the relatively narrow exit opening 42 of the guard column housing 45. Then, the mixture passes through a relatively large thru-bore section of the HPLC column 20. The sudden changes in the cross-sectional area of the flow path disrupt the flow of the mixture, cause unwanted mixing and blending of the mixture, and lower the capability of the HPLC column 20 to separate compounds from the mixture (i.e., causes band-spreading).

Below the guard column housing 45 is the HPLC column top seal 100 that is placed inside the top of the HPLC column 20. An HPLC column bottom seal 110 is placed between the HPLC column 20 and an exit fitting 375 that sheathes the exit apparatus 340. The exit fitting 375, when screwed onto a lower HPLC column fitting 365, holds the exit fitting 375 and the HPLC column 20 together with the use of two lower grommets 385 that fit into a lower groove 395. The end of the exit fitting 375 contains a pathway through which the components of the mixture travel before flowing into the exit apparatus 340, after which they can be measured, collected, redirected or disposed of.

The HPLC column bottom seal 110, the HPLC column top seal 100, and the guard column top seal 90 are typically formed from polymeric materials that are specifically designed and manufactured to withstand the high-pressure and potentially corrosive conditions necessary for HPLC processes. Hence, the seal materials are extremely expensive and each seal increases the overall cost of the HPLC apparatus illustrated in FIG. 2. In addition, the HPLC apparatus in FIG. 1 and in FIG. 2 both require the sample mixture to "funnel" through narrow channels between the guard columns and the HPLC columns. The sudden changes in the cross-sectional area of the flow path disrupt the flow of the mixture, cause unwanted mixing and blending of the mixture, and lower the capability of the HPLC column 20 to separate compounds from the mixture (i.e., causes band-spreading). Accordingly, a need exists for an improved HPLC apparatus 10.

BRIEF SUMMARY OF THE INVENTION

According to one embodiment, a high-pressure liquid chromatography (HPLC) apparatus that includes a top end fitting, a removable, metallic guard column in direct contact with the top end fitting, wherein the guard column includes a guard column inlet and a guard column outlet, and an HPLC column, wherein the HPLC column includes an HPLC column inlet and an HPLC column outlet, and wherein substantially all of the guard column outlet engages the HPLC column inlet.

According to another embodiment, an An HPLC apparatus that includes a hand-tightened top end fitting at a first end of the HPLC apparatus and a hand-tightened bottom end fitting at a second end of the HPLC apparatus wherein the top end fitting and the bottom end fitting provide seals sufficient for operation of the HPLC apparatus, and an HPLC column positioned between the top end fitting and the bottom end fitting, the HPLC column having an HPLC column inlet and an HPLC column outlet, a removable guard column having a guard column inlet and a guard column outlet wherein substantially all of the guard column outlet engages the HPLC column inlet.

According to yet another embodiment, a method of gathering HPLC data that includes hand-tightening a top fitting and a bottom fitting around a removable guard column and an HPLC column engaged with the guard column to provide a seal, injecting an experimental sample into the guard column, and allowing the experimental sample to travel through a path of substantially constant cross-sectional geometry as the experimental sample travels through a guard column outlet, to an HPLC column inlet, and through the HPLC column inlet.

BRIEF DESCRIPTION OF THE DRAWINGS

The invention will be described by way of example, in the description of exemplary embodiments, with particular reference to the accompanying drawings in which.

DETAILED DESCRIPTION OF THE INVENTION

Figure 3:
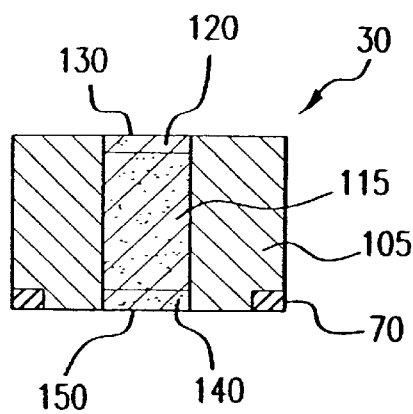
FIG. 3 illustrates a cross-sectional view of a guard column used in HPLC columns within the scope of the present invention.

FIG. 3 illustrates a guard column 30 for use with an HPLC apparatus 10. The guard column 30 includes a thru-bored guard column grooved body 105 with a diametral groove capable of accommodating the presence of a guard column bottom seal 70.

The guard column bottom seal 70, and all other seals of the present invention, can be made of any material(s) capable of preventing leaking under the conditions necessary to conduct the high-pressure liquid chromatography (HPLC) process. Preferred materials include perfluoroelastomers such as, for example, CHEMRAZ and KALREZ perfluoroelastomers. All seals of the present invention are also preferably, though not necessarily, substantially square cross-sectional quad-ring seals.

Inside the thru-bored section of the guard column grooved body 105 is the guard column packing 115. The guard column packing 115 is kept in place between a porous guard column top frit 120 at a guard column inlet 130 and a porous guard column bottom frit 140 at a guard column outlet 150. The materials from which all of the packings 115, 170 and porous frits 120, 140, 180, 200 of the present invention are made are those materials that allow for HPLC processes to be carried out. They include, but are not limited to, silane-derivatized silica particles for the packings 115, 170 and to porous stainless steel for the frits 120, 140, 180, 200.

Figure 4:
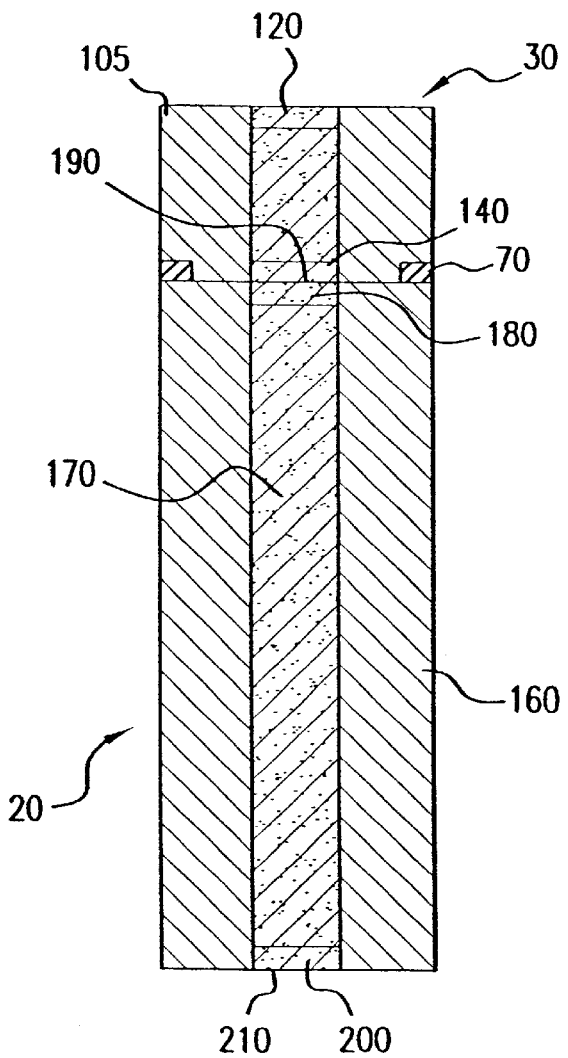
FIG. 4 illustrates a cross-sectional view of a guard column and of an HPLC column connected to it, wherein the HPLC column top frit and the guard column bottom frit have substantially similar diametral cross-sectional geometries.

FIG. 4 illustrates a portion of an HPLC column 20 and how it is arranged relative to the guard column 30 according to one embodiment of the present invention. According to the embodiment shown, the HPLC column 20 includes an HPLC column body 160 with HPLC column packing 170 contained within it. The HPLC column packing 170 is kept in place between a porous HPLC column top frit 180 at the HPLC column inlet 190 and a porous HPLC column bottom frit 200 at the HPLC column outlet 210.

Because the guard column bottom seal 70 is positioned within the guard column grooved body 105 instead of below the guard column 30, the guard column bottom frit 140 can be placed in direct contact with the HPLC column top frit 180. Hence, the guard column 30 and HPLC column 20 are directly connected or engaged to each other, eliminating the need for a capillary connector 40 or guard column housing 45.

According to other embodiments of the present invention, the guard column bottom frit 140 and the HPLC column top frit 180 are not quite in direct contact. Instead, any or all of the frits 120, 140, 180, 200 are proximate (e.g., within 0.1 millimeters) of the column inlets and outlets to which they are closest to, but are not quite flush with the inlet or outlet. These embodiments allow for greater manufacturing tolerances.

In other embodiments of the present invention, items such as, but not limited to, washers and additional seals can be placed between the guard column 30 and the HPLC column 20, causing the guard column bottom frit 140 and the HPLC column top frit 180 to be slightly separated. However, such items do not prevent the guard column outlet 150 from engaging with the HPLC column inlet 190. Even with, for example, the presence of a washer, the guard column outlet 150 and the HPLC column inlet 190 can still come together and/or interlock to an extent sufficient to maintain the capability of the HPLC apparatus to separate compounds from the mixture with minimum band-spreading.

Figure 1:
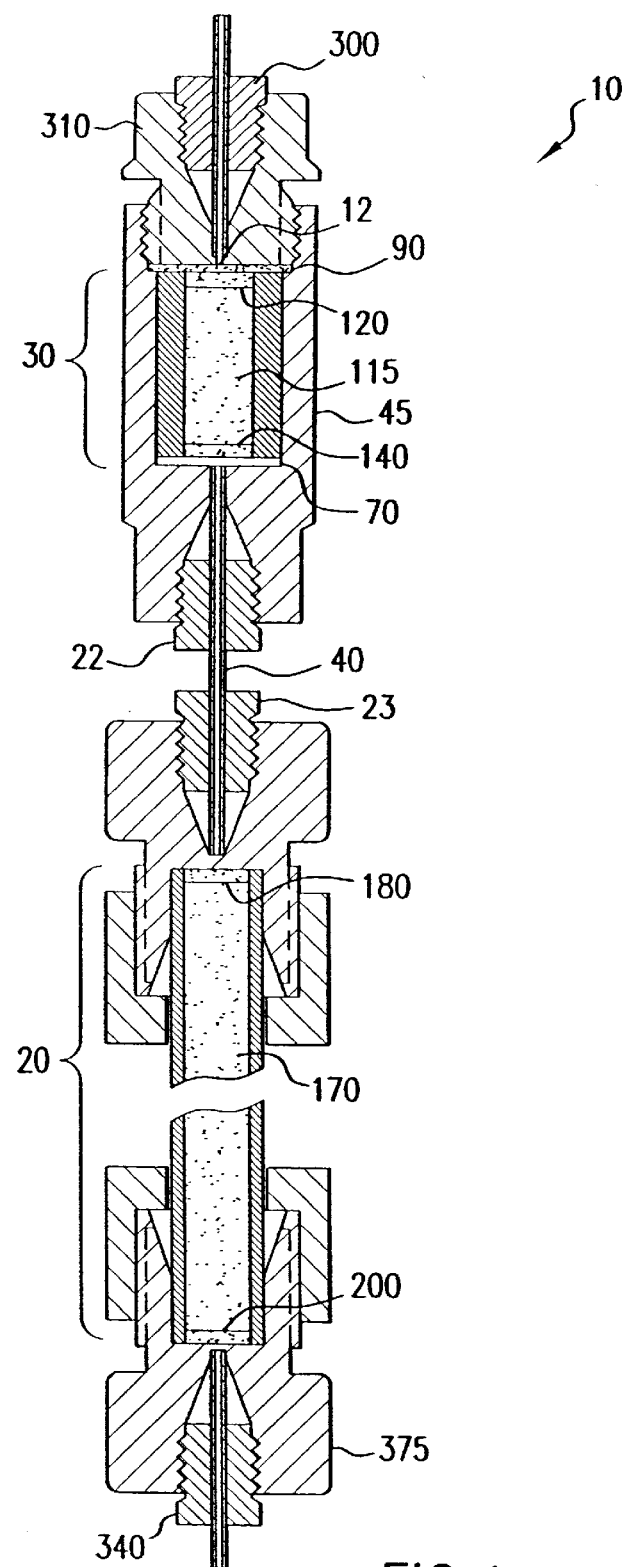
FIG. 1 illustrates a cross-sectional view of a high-pressure liquid chromatography (HPLC) apparatus incorporating a non-integral guard column according to the related art.
Figure 2:
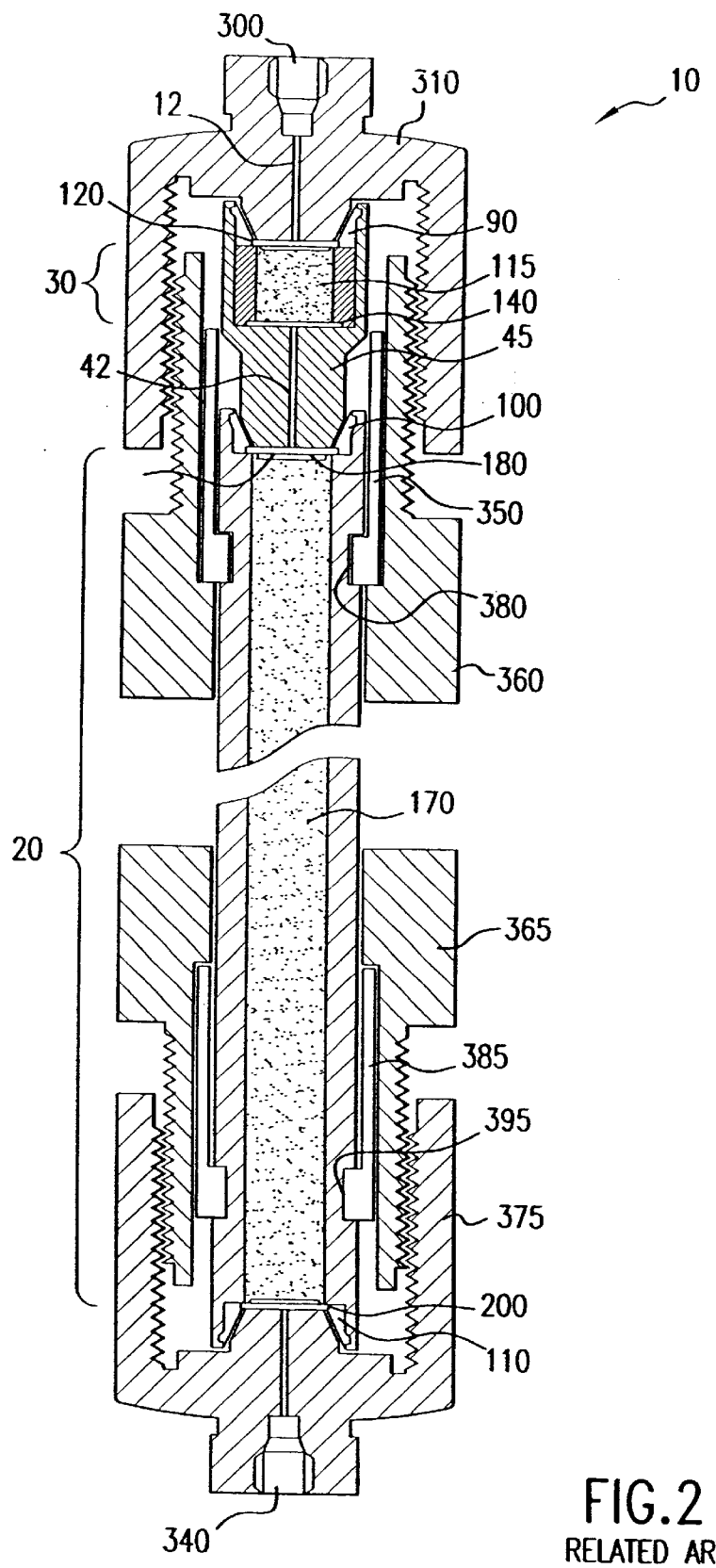
FIG. 2 illustrates a cross-sectional view of an alternative liquid chromatography (HPLC) apparatus incorporating an integral guard column according to the related art.
Figure 5:
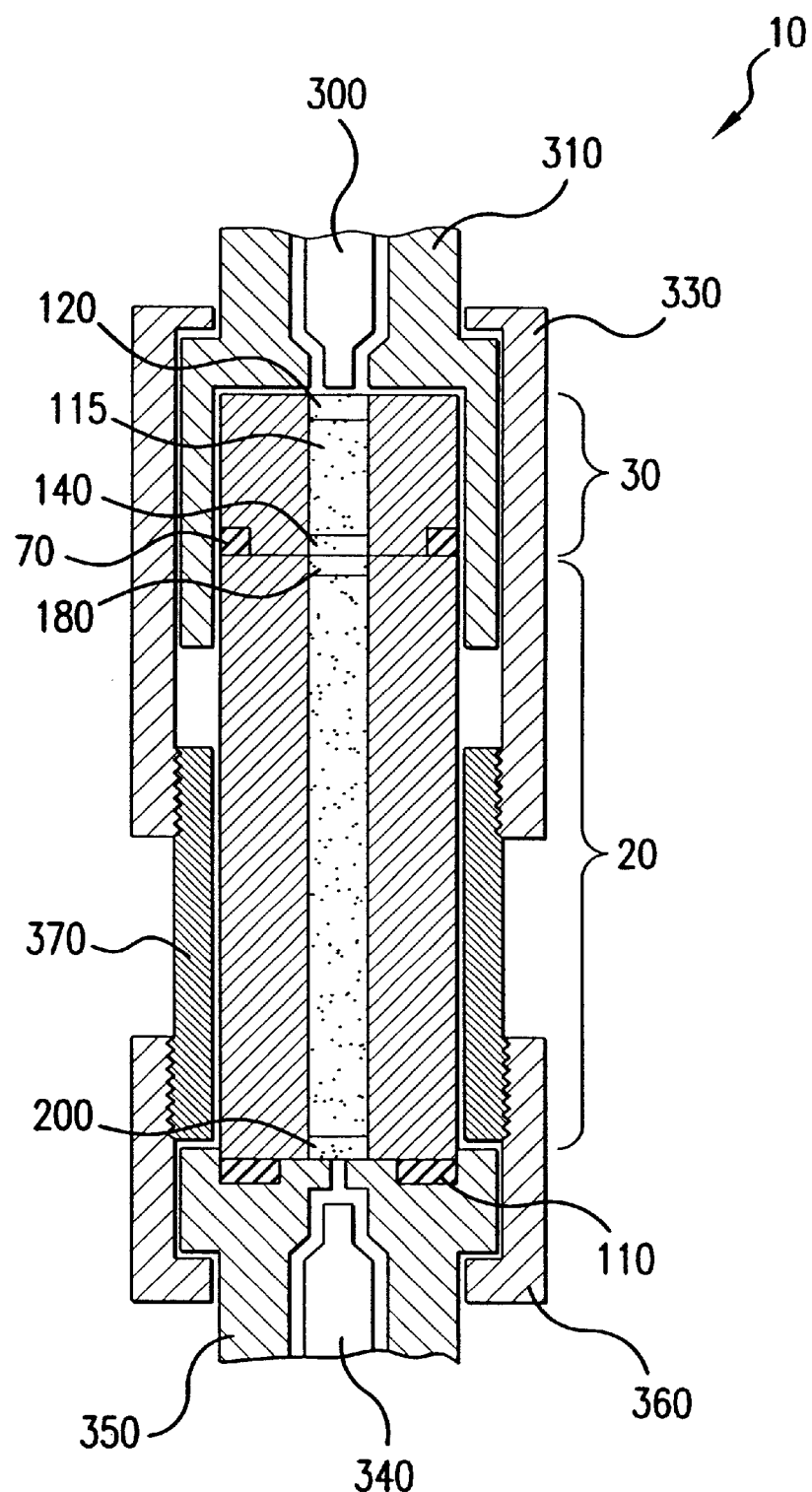
FIG. 5 illustrates a cross-sectional view of a first embodiment of an HPLC apparatus according to the present invention.

The HPLC column 20 and guard column 30 illustrated in FIG. 4 are illustrated in FIG. 5 within a simpler design for an HPLC apparatus 10. The HPLC apparatus 10 in FIG. 5 requires fewer seals than the designs in FIG. 1 or FIG. 2 and therefore reduces the overall cost of the HPLC apparatus 10. Also, without the constrictive openings of the capillary connector 40 or guard column housing 45, the mixture does not have to experience a sudden widening of the flow path as it enters the HPLC column 20. Instead, according to the embodiments of the present invention illustrated in FIG. 5, the guard column bottom frit 140 and the HPLC column top frit 180 have identical diametral cross-sectional dimensions and geometries with relation to the flow path of the mixture.

According to the embodiment of the present invention illustrated in FIG. 5, only two seals, the guard column bottom seal 70 and an HPLC column bottom seal 110, are needed to prevent leaking. Hence, the cost of the HPLC apparatus 10 shown in FIG. 5, and the cost of the subsequent maintenance for it, is substantially reduced when compared to an HPLC apparatus 10 where three or more seals are used.

The HPLC apparatus 10 illustrated in FIG. 5, along with other embodiments of the present invention, has the advantage that the top end fitting 330 and the bottom end fitting 360 can usually be screwed onto a spacer 370 by hand-tightening. Even under 6,000 psi internal operating conditions, no wrenches are typically needed to tighten the fittings 330, 360 sufficiently to prevent leaking in the HPLC apparatus 10. In fact, for one embodiment of the present invention wherein the HPLC column 20 had a 0.250-inch outer diameter, the amount of force needed to prevent leaking was approximately 0.5 foot-pounds. For another embodiment of the present invention wherein an HPLC column 20 with a 1.0-inch outer diameter, 2 foot-pounds of force were required, an amount of force well within the capability of human hands.

Figure 6:
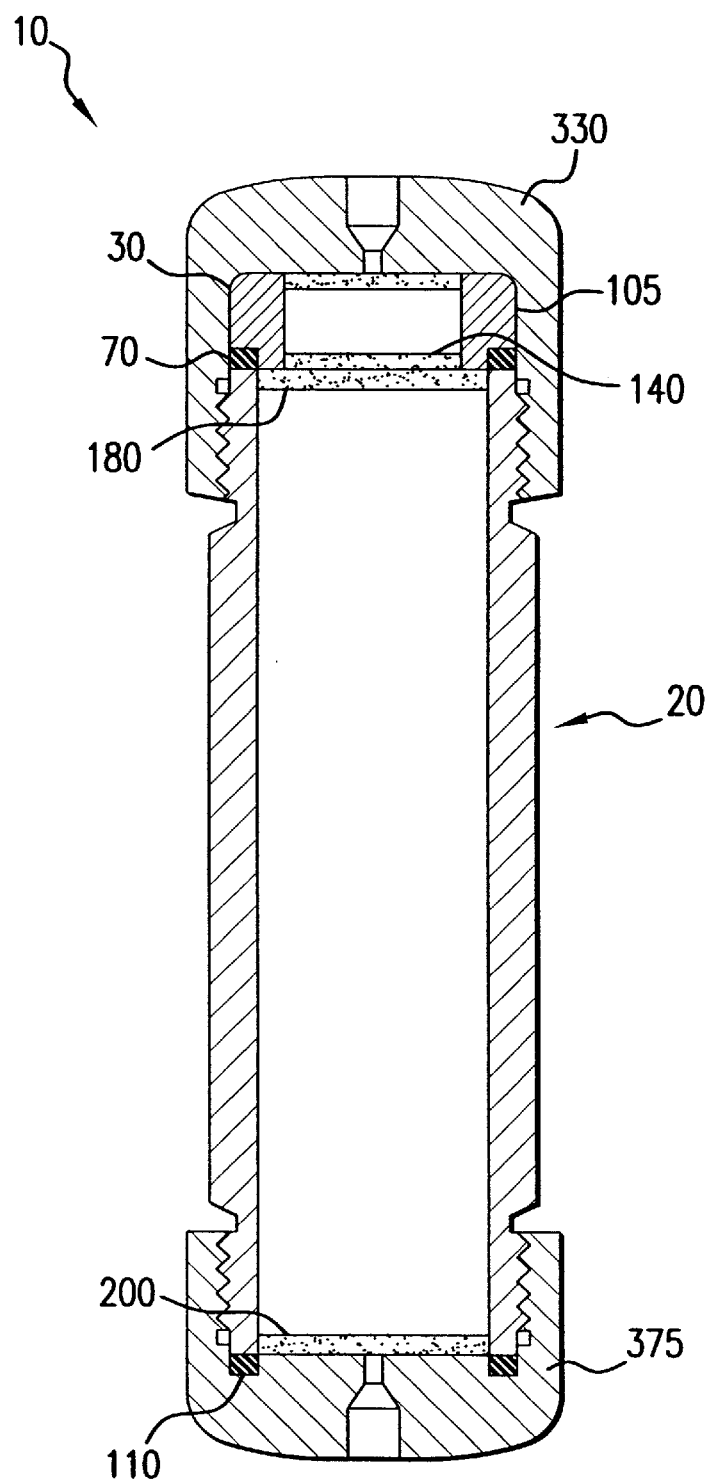
FIG. 6 illustrates a cross-sectional view of a guard column and of an HPLC column connected to it, wherein the HPLC column top frit and the guard column bottom frit have different diametral cross-sectional geometries.

FIG. 6 illustrates another embodiment of the present invention wherein a guard column 30 and an HPLC column 20 are in direct contact with each other and where only one seal, a guard column bottom seal 70, is placed between them. Although a guard column grooved body 105 is illustrated in FIG. 6, other embodiments of the present invention make use of an HPLC column grooved body 150 and use an HPLC column top seal as the only seal between the guard column 30 and the HPLC column 20.

According to the apparatus illustrated in FIG. 6, the guard column bottom frit 140 is smaller than the HPLC column top frit 180. This embodiment of the present invention minimizes the costs of the HPLC apparatus 10 because it utilizes only a single seal between the HPLC column 20 and the guard column 30.

The embodiment illustrated in FIG. 6 also shows that the spacer 370 illustrated in FIG. 5 is not always required. According to the embodiment illustrated in FIG. 6, the top end fitting 330 and the bottom end fitting 360 are both screwed directly onto a threaded HPLC column 20.

The foregoing detailed description has been given for understanding exemplary implementations of the invention only and no unnecessary limitations should be understood therefrom as modifications will be obvious to those skilled in the art without departing from the scope of the appended claims and their equivalents.

What is claimed is:

1. An HPLC apparatus comprising:
    a hand-tightened top end fitting at a first end of the HPLC apparatus and a hand-tightened bottom end fitting at a second end of the HPLC apparatus wherein the top end fitting and the bottom end fitting provide seals sufficient for operation of the HPLC apparatus;
    an HPLC column positioned between the top end fitting and the bottom end fitting, the HPLC column having an HPLC column inlet and an HPLC column outlet; and
    a removable guard column having a guard column inlet and a guard column outlet wherein substantially all of the guard column outlet engages the HPLC column inlet.

2. The HPLC apparatus of claim 1, wherein the HPLC column is threaded.

3. The HPLC apparatus of claim 1, wherein the guard column comprises a metallic portion.

4. The HPLC apparatus of claim 1, wherein the guard column is sealed to the HPLC column via a guard column bottom seal which has a substantially square cross section and engages a groove.

5. The HPLC apparatus of claim 4, wherein he guard column bottom seal comprises a perfluoroelastomer.

6. The HPLC apparatus of claim 1, further comprising an HPLC column bottom seal between the HPLC column and the bottom end fitting.

7. The HPLC column of claim 6, wherein the HPLC column bottom seal comprises a seal ring having a substantial square cross section.

8. The HPLC column of claim 6, wherein the HPLC column bottom seal comprises a perfluoroelastomer.

9. An HPLC apparatus comprising:
    a removable guard column which includes a guard column inlet and a guard column outlet; and
    an HPLC column which includes an HPLC column inlet and an HPLC column outlet, wherein substantially all of the guard column outlet engages the HPLC column inlet, and wherein the guard column is sealed to the HPLC column via a hand-tightenable seal which comprises a seal ring engaging a groove.

10. An HPLC apparatus comprising:

a hand-tightenable top end fitting at a first end of the HPLC apparatus and a hand-tightenable bottom end fitting at a second end of the HPLC apparatus wherein the top end fitting and the bottom end fitting provide seals sufficient for operation of the HPLC apparatus;

an HPLC column positioned between the top end fitting and the bottom end fitting, the HPLC column having an HPLC column inlet and an HPLC column outlet; and a removable guard column having a guard column inlet and a guard column outlet wherein substantially all of the guard column outlet engages the HPLC column inlet, and wherein the guard column is sealed to the HPLC column via a seal ring which has a substantially square cross section and engages a groove.

11. The HPLC apparatus of claim 10, wherein the HPLC column is threaded.

* * * * *